United States Patent [19]

King

[11] Patent Number: 5,103,821
[45] Date of Patent: Apr. 14, 1992

[54] METHOD OF PROVIDING A BIOLOGICAL PACEMAKER

[75] Inventor: Wendell L. King, North Oaks, Minn.

[73] Assignee: Angeion Corporation, Plymouth, Minn.

[21] Appl. No.: 622,381

[22] Filed: Nov. 30, 1990

Related U.S. Application Data

[63] Continuation of Ser. No. 319,094, Mar. 6, 1989, abandoned.

[51] Int. Cl.$^5$ .............................................. A61N 1/00
[52] U.S. Cl. .................................... 128/419 P; 600/36
[58] Field of Search .............. 128/333, 419 P; 600/33, 600/35, 36

[56] References Cited

U.S. PATENT DOCUMENTS

| | | | |
|---|---|---|---|
| Re. 31,305 | 9/1982 | Hancock et al. | 8/94.11 |
| 3,707,958 | 1/1973 | Sparks | 128/1 R |
| 3,710,777 | 1/1973 | Sparks | 128/1 R |
| 3,866,247 | 2/1975 | Sparks | 3/1 |
| 3,866,609 | 2/1975 | Sparks | 128/303 |
| 4,173,689 | 11/1979 | Lyman et al. | 521/64 |
| 4,378,224 | 5/1983 | Nimni et al. | 8/94.11 |
| 4,770,665 | 9/1988 | Nashef | 8/94.11 |
| 4,791,911 | 12/1988 | Magovern | 600/36 |
| 4,928,689 | 5/1990 | Hauser | 128/419 P |

OTHER PUBLICATIONS

Chandler McC. Brooks, et al., The Sinoatrial Pacemaker of the Heart, pp. 3–9, 20–23.

William J. Marvin, Jr., et al., "The Isolated Sinoatrial Node Cell in Primary Culture from the Newborn Rat", *Circulation Research*, vol. 55, No. 2, Aug. 1984, pp. 253–260.

Richard D. Nathan, "Two Electrophysiologically Distinct Types of Cultured Pacemaker Cells from Rabbin Sinoatrial Node", *Rapid Communications*, 1986, pp. H325–H329.

Robert M. Sade, et al., "Myocyte Transplantation for Treatment of Complete Heart, Block", *Surgery*, Apr. 1985, pp. 495–497.

Yasuo Morishita, et al., "Sino–Atrial Node Transplantation in the Dog", *So. Vasc. Surg.*, 15(6), 1981, pp. 388–393.

T. E. Starzl, et al., "Failure of Sino–Atrial Nodal Transplantation for the Treatment of Experimental Complete Heart Block in Dogs", *Journal of Thoracic and Cardiovascular Surgery*, Jul.–Dec., 1963, vol. 46, pp. 201–206.

Richard W. Ernst, et al., "Pedicle Grafting of the Sino–Auricular Node to the Right Ventricle ofr the Treatment of Complete Atrioventricular Block", *Journal of Thoracic and Cardiovascular Surgery*, vol. 44, Jul.–Dec. 1962, pp. 681–686.

Arthur J. Vander, et al., *Human physiology, the Mechanisms of Body Function*, pp. 267–269.

*Primary Examiner*—Francis Jaworski
*Assistant Examiner*—George Manuel
*Attorney, Agent, or Firm*—Hugh D. Jaeger

[57] ABSTRACT

A process for providing a biological pacemaker for the human heart wherein the sino-atrial (S-A) node cells are removed from the heart and cultured to generate a critical mass of S-A node cells of sufficient quantity to generate a depolarization wave capable of stimulating the cells of the myocardium to ensure normal or near-normal pumping action in the heart. The critical mass of S-A node cells are then implanted in the myocardial tissue of the right ventricle to provide biological pacing for the heart which is sensitive to and variable with normal increase and decrease of output demands on the heart.

31 Claims, 1 Drawing Sheet

METHOD OF PROVIDING A BIOLOGICAL PACEMAKER

This is a continuation of application Ser. No. 07/319,094, filed Mar. 6, 1989, now abandoned.

BACKGROUND OF THE INVENTION

A major cause of death and poor health in significant segments of the population in the United States and in many other areas of the world involve disease and insufficient function of the heart. The vitality of all tissues in the body depends upon a continual flow of blood at an adequate rate to permit efficient and satisfactory function of the organs. The heart is required to function at a relatively high level. The heart typically pumps 75 gallons of blood per hour when the body is at rest and is required to function at even higher rates during moderate or heavy levels of exertion and activity.

Interruption or interference with the continuous and efficient function of the heart can occur for a variety of reasons. The arteries of the heart may become diseased and obstructed with the result that the heart will either develop insufficient blood flow or blood flow will become terminated. This arteriosclerosis is the well-known coronary artery disease that is a leading killer of some segments of the population, especially men.

Diseased coronary arteries often provide restricted circulation and diminished blood flow with the result that the heart is unable to carry out its normal function as it is gradually starved for blood. The result is that the heart fails to contract as forcefully as necessary with the result that the entire body suffers from insufficient blood flow.

When one of the coronary arteries becomes plugged by a blood clot, that particular area of the heart served by the plugged coronary artery will be cut off from an adequate supply of blood and, if circulation is not immediately resumed, the muscle tissue of that particular area of the heart will become impaired or die.

Insufficient or terminated blood flow in certain areas of the heart can also have deleterious effect on other functions of the heart, including the conduction system of the heart. The conduction system of the heart is a group of structures within the heart that determine heart rate in response to influences from the nervous system as well as the chemical information carried to the heart from other organs of the body. The conduction system provides stimulating impulses to all parts of the myocardium in a coordinated fashion. The coordination of the impulses is important to ensure that the different sections of the heart act in coordination to pump blood throughout the body. Coordinated function of the heart contraction ensure delivery of an adequate supply of blood to the various organs as demands on the organs vary. The stimulations necessary for proper excitation of the myocardium need to be coordinated to ensure the heart contracts effectively to make the heart an effective fluid pump.

The conduction system in the heart depends upon a regular generation of a depolarization wave of adequate magnitude to cause the myocardium to contract in an orderly fashion to force blood through the body's veins and arteries. The proper function of the heart is dependent upon the ability of the heart to generate or start a depolarization wave at a particular location in the heart in order to ensure a proper contraction. This depolarization wave must be generated in a place, at a location and with a frequency which is responsive to the needs of the heart as well as the other functions of the body.

The depolarization wave of the heart is generated as a result of some unique characteristics of myocardial tissue. Depolarization occurs as cell tissue, either muscle or nerve cells, is stimulated. The stimulus is then transmitted to the next cell in a process which is called depolarization. Through this process, a depolarization wave can be generated in a mass of muscle tissue with the result that the muscle tissue responds to the stimulus. This response results in the familiar muscle function or heart beat of the heart.

It has been learned that the generation of this depolarization stimulus is a characteristic of the behavior of the cell membrane of individual cells of living tissue. Living cells selectively permit the passage of various substances such as nutrients, oxygen, waste products through the cell membrane. These substances move freely through the cell membrane in order to ensure the adequate nutrition of the cell and maintain the life function of the cell. While there is a free movement of substances through the cell membrane, the movement is by no means unrestricted. Certain essential substances are blocked by the cell membrane so that certain essential substances are not permitted to move outside of the cell.

Other substances are not permitted to move from outside of the cell to the interior of the cell with the result that there is a substantial selectivity which occurs at the cell membrane preventing movement of selected elements through or across the cell membrane depending upon the nature of the substance. As an example, this selective permeability at the cell membrane works to keep substances such as potassium inside the cell and, at the same time, keep sodium out of the cell. Examination of the function of these two elements has revealed that they are instrumental in the proper function of heart cells and, indeed, are probably the basis for the generation of a depolarization wave necessary to stimulate heart beat in myocardial tissue.

When myocardial tissue cell is at rest, the concentration of sodium, which carries a positive electrical charge, on the outside of the cell membrane is about equal to the potassium concentration inside the cell membrane. When the cell is at rest and when the concentration of sodium and potassium on either side of the cell membrane are approximately equal, a balanced condition occurs in which essentially no activity occurs. In a normal cell, a relatively large number of substances carry a negative charge. These negatively charged substances are of a type which are retained within the cell by the selective permeability of the cell membrane. As a result, there normally are more negatively charged particles or substances inside the cell membrane than occur on the outside of the cell membrane. This results in a condition in which the inside of the cell membrane is more negatively charged than the outside of the cell membrane. This charge difference results in a voltage drop across the cell membrane that can be measured by sophisticated scientific equipment.

Measurement of the voltage drop across the cell membrane will reveal that the inside of the membrane is negatively charged with respect to the outside of the membrane. In this condition, the cell is polarized.

The polarized condition of the cell membrane normally exists uniformly throughout the cell membrane except when the cell membrane is disturbed or stimulated at a particular location. When a stimulant of selected types is applied to the cell membrane, the membrane loses its selective permeability at that particular site with the result that substances which normally are inhibited from moving across the cell membrane is lost. The cell membrane therefore no longer blocks the entrance of such a substance across the cell membrane. In such instances, the cell membrane does not block the entrance of sodium located outside of the cell. Sodium can then move to the interior of the cell. The stimulus capable of causing the cell membrane to lose its selective permeability characteristic can include a stimulus such as electrical, mechanical or thermal.

It has been found that, when the cell membrane is stimulated, sodium at the stimulated site rushes through and across the cell membrane flooding the interior of the cell with sodium at that particular location. This inrush of sodium further disturbs the membrane adjacent the original site of stimulation so that these adjacent areas of membrane also lose the property of selective permeability with the result that additional sodium is admitted over a wider area of the cell membrane. This progressively enlarged disturbance of the cell membrane expands outwardly from the original site of stimulation with the result that sodium enters in a wider and wider area in what appears to be an expanding wave front of stimulation originating from the original site of stimulation.

Finally, this progressive increase in the stimulation and the progressive loss of selective permeability progresses down the entire length of the cell to the end of the cell at which point the interior of the cell is flooded with sodium. Since sodium carries a positive charge, the negative charge on the cell interior is essentially neutralized so that the cell is then said to be depolarized. This depolarization upsets the steady state or relaxed condition of the cell interior and affects the myofibrals of the cell. Myofibrals are the strings of protein running the length of the cell. The depolarization of the interior of the cell causes the myofibrals to shorten with the result that the entire cell contracts or shortens in response to the depolarization.

As the cell depolarizes, potassium moves through the cell membrane to the outside of the cell. While the potassium exits through the cell membrane, the cell membrane also begins to pump sodium out of the cell. As the positively charged particles of sodium leave, the inside of the cell membrane again starts to become negative again. This reestablishment of the normal negative state in the interior of the cell continues until the original state of the cell is restored and the inside of the cell is again negative with respect to the outside of the cell. When this restoration of the negative condition of the cell occurs, the cell begins to relax and becomes repolarized. Thus, it is apparent that the cell in a repetition of this process undergoes a cycle of contraction and relaxation or depolarization and repolarization as a normal function.

This cycle occurs not in just one of the cells but occurs in all of the cells which are neighbors of the originally stimulated cell. A stimulated cell will pass on the depolarization to its neighbor cells with the result that a depolarization wave will radiate from an original site of stimulation, be it electrical, chemical or mechanical, in a wave pattern throughout a muscle group such as that represented by the heart. This depolarization wave creates a contraction of the muscle tissue in a wave pattern so that the pattern moves through the cells of the myocardium in a uniform and progressive manner, thus generating the pumping action which is characteristic of a healthy heart.

It was this characteristic of the heart muscle to react to electrical and mechanical stimulation which led A. S. Hyman to develop a machine for ambulance use in the 1930's which could be used to stimulate heart beat in accident victims. Hyman is credited with stating the principles of pacing through the use of small electrical stimulus applied to a relatively small area to give a rise to a contraction wave which spreads throughout the entire heart muscle giving the heart a relatively normal contraction. The device which Hyman developed included an electrode needle which could be passed through the ribs of a patient and into the heart for applying the electrical stimulus.

Later clinical work undertaken by Zoell advanced the understanding of the pacing process. In 1952, he used skin electrodes applied to the patient's chest to transmit an electrical shock to the heart causing it to contract. This work and other work proved to have lifesaving value and sparked interest in investigating the use of pacing. The result of this work has evolved to the point where, today, electro-mechanical pacemaker devices are routinely implanted in the muscle of the heart in order to apply a regular stimulus to the heart to set up regular heart beat in those patients having inadequate heart pacing function and thus ensuring better function of the heart as a fluid pumping mechanism.

The currently used electronic pacemakers are typically battery powered with the batteries having an average longevity of about five years. Typically, the electro-mechanical pacemaker is implanted in the heart by positioning an electrode in the apex of the right ventricle and the remainder of the pacemaker, including the battery, is implanted under the skin of the patient's chest. This operation is a relatively expensive implant procedure which is satisfactory for the life of the batteries used in the device. When the batteries are exhausted, the battery cannot be replaced and, in the typical patient, the entire pulse generator must be replaced. The cost of the replacement of the pacemaker is nearly the same as the original cost of implant.

As with any mechanical and electrical device, there are a number of problems which might be encountered with the device which will require remedial surgery. Batteries, as an example, might prematurely fail. Further, the generator may fail to provide proper electrical pulses to stimulate the heart muscle as needed. The typical electro-mechanical pacemaker includes sophisticated microelectronics which can prematurely fail. Further, the hermetically sealed pulse generator can develop a leak which will result in a short of the electrical circuitry necessary to the function of the generator.

The electro-mechanical pacemaker also employs a long flexible lead which extends from the pacemaker through the heart to the site of the implant of the electrode used to stimulate the heart muscle. This lead is subject to constant flexing with the risk that the flexing will ultimately result in a break in the lead.

Mechanical pacemakers also depend upon the success with which the electrode remains implanted in the right ventricle to stimulate the myocardial tissue. If the electrode should become disengaged, it would immediately result in misfunction or failure of the function of the pacemaker.

The need to implant the electrode in the heart in a secure fashion also includes a further problem of ensuring that the electrode remains in place without causing inflammation or rejection by the body tissue. Typically, the body will attempt to reject any foreign tissue or material which is imbedded in the tissues of the body. This rejection reaction can produce a systemic rejection process which will require removal of the electrode. Further, the imbedded electrode always presents the risk of infection in the muscle tissue with the potential for causing serious, if not fatal, trauma to the heart muscle.

A further disadvantage of the currently employed electro-mechanical pacemaker is the lack of an effective mechanism for detecting changes in demand for oxygen by the organs of the body. These electro-mechanical pacemakers stimulate the heart and generate the depolarization wave at a predetermined rate. This rate does not increase in response to increased demand by the organs of the body in the way natural pacing changes in the heart. Consequently, electro-mechanical pacemakers tend to place limitations on the level of physical activities of the user.

Accordingly, while great advances have been made in the pacing process employing effective mechanical processors, the use of such electro-mechanical pacers nevertheless pose substantial risks and disadvantages for the patient.

SUMMARY OF THE INVENTION

It is an object of this invention to provide a process for utilizing a biological pacemaker to ensure proper pacing of the heart.

The process of the present invention is designed to take advantage of cell culture techniques in order to provide a natural culture of sino-atrial (S-A) node cells which may be implanted in the right ventricle of the heart to generate depolarization waves in myocardial tissue.

The present invention provides a process for selecting healthy S-A node cells in the heart which are then cultured to a sufficiently large mass to generate a depolarization wave in myocardial tissue. The mass of S-A node cells is then implanted in the right ventricle of the heart where the implanted S-A node cells undertake generation of a depolarization wave of sufficient magnitude to stimulate the generation of contraction of the heart muscle to ensure proper function of the myocardium.

The present process provides a method for providing a biological pacemaker capable of responding to changes in the oxygen and other systemic demands of the heart and other body organs so that, as the oxygen demands of the other organs is increased, the mass of implanted S-A node cells receive stimulation from such demands and changes the frequency of the generation of a depolarization wave to increase the pace at which the muscles of the heart contract.

The process of this invention provides a method for implanting a mass of S-A node cells in the right ventricle of the heart which will avoid rejection by the body and avoid mechanical failure typical of electro-mechanical pacers currently used in the pacing of hearts.

The present invention contemplates a process whereby a mass of S-A node cells is harvested from the area of the heart in the right atrium where such S-A node cells are located. The harvested S-A node cells are then cultured either in vitro or within the body' of the patient for a sufficient time to grow a sufficiently large mass of S-A node cells capable of generating a depolarization wave of adequate magnitude to stimulate the heart to produce contractions. The S-A node cells are implanted in the right ventricle of the heart, preferably near the apex of the right ventricle, to generate a depolarization wave capable of stimulating the ventricles in a wave pattern which simulates the natural contraction of the heart muscle.

Preferably the S-A node cells used in the process are harvested from the patient who will later receive the implant of the newly grown S-A node cells in order to prevent any tissue rejection which may occur from the use of unrelated or nonbiological components.

In the process, the S-A node of the patient is identified and mapped after which the S-A node cells are removed for growth. After the newly grown S-A node cells are implanted in the right ventricle of the heart, the previously mapped or identified area of node cells naturally occurring in the right ventricle can be destroyed in order to prevent "cross-talk" between the newly implanted S-A node cells and those remaining in the right atrium.

The process of the present invention contemplates harvesting S-A node cells from the heart of a patient who will also be the recipient of the culture growth of such cells. In one variation of the process, a temporary electro-mechanical pacemaker is implanted in the patient's heart while the harvested S-A node cells are being cultured to create a critical mass of cells necessary to generate a depolarization wave of adequate magnitude to support normal contraction in the myocardium.

These and other features of the process will be more readily understood by a reference to the following drawing.

DRAWINGS

FIGURE 1 of the drawings is a cross-sectional view of the chambers of the heart illustrating the location of the S-A node cells and the preferred site of implantation of a biological pacemaker according to the present process.

DETAILED DESCRIPTION OF THE INVENTION

Figure 1:
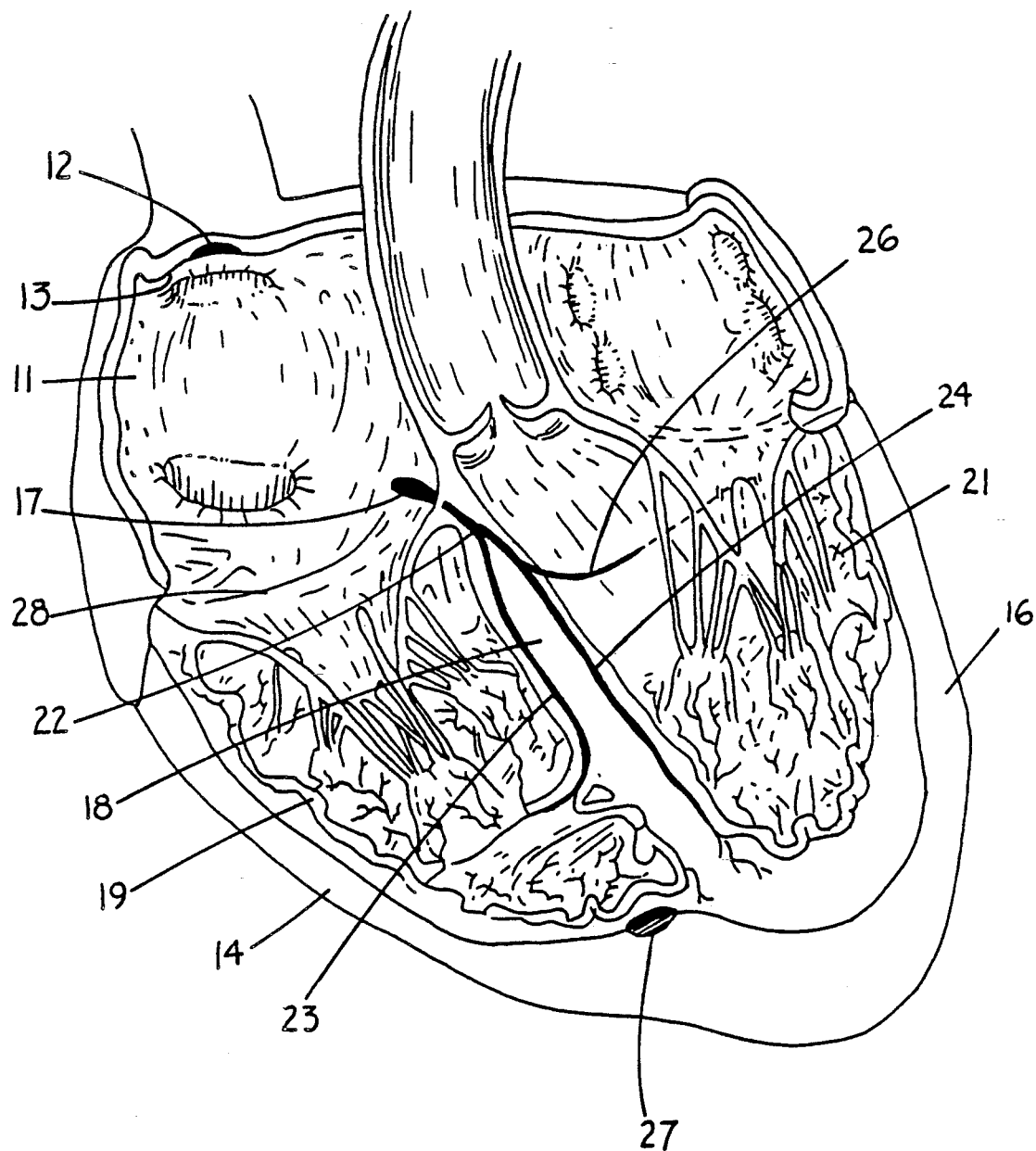

Refer first to FIGURE 1 of the drawings which illustrates a cross-sectional view of the chambers of the heart. This is a view of the heart as it would normally lie in the chest of a patient. The right atrium 11 is the site of the S-A node cells 12 which are responsible for pacing the heart in a normally functioning heart. These S-A node cells are a small knot of cells buried within the roof 13 of the right atrium 11 and communicate directly with the surrounding atrial muscle cells.

This small knot of S-A node cells 12 is responsible for generating the initial depolarization wave which ultimately results in the contraction of the entire heart muscle and, in particular, the heart muscle forming the wall 14 of the right ventricle 19 and the wall 16 of the left ventricle 21 of the heart. In a typical cycle of the heart, the S-A node cells 12 would initiate a depolarization wave which spreads through the muscle tissue of the right atrium until the wave front arrives at another small knot of cells in the right atrium identified as atrial ventricular (A-V) node 17. The A-V node 17 is located low in the rear wall of the right atrium 11 and passes downwardly within wall 18 which separates the right ventricle 19 from the left ventricle 21. The long fibers 22 which extend into wall 18 are long cell fibers which are much like typical nerve cells. These long fibers 22 form a bundle of fibers known as the Bundle of His and extend from the A-V node 17 along the length of wall 18 and into all of the parts of the ventricular myocardium. It is noted that the Bundle of His 22 branches at numerous points to provide stimulation to the muscles of both the right ventricle 19 and the left ventricle 21.

Proper function of the heart through contraction of the left and right ventricles is dependent upon a depolarization wave radiating from the S-A node 12 through the right atrial and along the Bundle of His 22 where the depolarization wave stimulates the myocardium of the left and right ventricle low in the heart to ensure that the depolarization or contraction of the muscle tissue progresses in a wave pattern which will produce a pumping action in the left and right ventricles.

When disease in the heart results in impaired function in the S-A node 12 or if the diseased heart causes damage or interruption in the atrium surrounding the A-V node 17 so that depolarization does not reach the A-V node 17, then interruption of the depolarization wave to the left and right ventricles 21 and 19 occurs. Frequently, fractures may also occur in the Bundle of His 22 or in the bundle branches 23, 24 or 26 with the result that the depolarization wave generated by the S-A node 12 likewise does not reach the right and left ventricles 19 and 21 in a uniform and efficient fashion. In severe cases, there will be a complete heart blockage of the depolarization wave. Since potential pacemaker cells are scattered throughout the heart, the heart may not stop pumping at this point; however, the secondary pacemaker cells may generate depolarization waves which are out of synchronization and thereby cause improper rhythm in the contraction of the myocardium. The result is a heart which becomes an inefficient and ineffective fluid pump.

Furthermore, where a complete blockage occurs, the potential pacemakers cells, if located very low in the ventricles, will generate a pulsing rhythm which is very slow, frequently in the area of 30–40 beats per minute, which is inadequate for normal exercise by a patient. While such secondary pacing may be adequate to sustain life, it certainly is not adequate for proper functioning of the other organs of the body and will eventually cause deterioration in those organs.

It will be apparent from the above description of the function of the S-A node 12 and the A-V node 17 that, if conduction of the depolarization wave does not occur in an organized and timely fashion, the pulsing of the heart will not occur properly. Interruption of the conduction due to broken branches, diseased A-V node and similar conduction problems will interrupt normal progression of a depolarization wave along normal pathways with the result that any contraction of the heart muscle will be distorted and less effective. Frequently, improper conduction of the depolarization wave and interference with secondary depolarization generation will result in retrograde conduction. Impulses thus move in opposite directions from normal with the result that the heart muscles function in an erratic and inefficient manner.

Also, if the S-A node cells 12 are diseased or improperly functioning, the cells will frequently generate a depolarization wave which is erratic or which has a rhythm which is unreliable. This could, as noted, result in secondary pacing sites generating waves which are out of synchronization. As a result, the heart will begin beating with abnormal rates or at rates which are substantially lower than adequate for proper flow of blood through the body.

The process for correcting the generation of depolarization waves adequate to ensure adequate and coordinated generation of depolarization waves first includes the identification of the location of the S-A node cells 12 in the right atrium 11. This first step in the process includes introducing a catheter using well-known techniques into the right atrium 11 of the heart. Typically, this catheter is introduced into the right atrium 11 by accessing the heart through the cephalic vein in or near the right shoulder of the patient. The catheter is passed through the cephalic vein into the sublairian vein and into the right ventrical. Typically, an introducer will be placed in the vein to permit repeated access to the right atrium 11. The introducer is a mechanical device designed to access a vein so that successive introduction of different catheters may be introduced into the vein for accomplishing several procedures necessary to carry out the process of this invention.

The first step in the process is to introduce a locating or mapping catheter into the right atrium 11. The locating o mapping catheter may be a catheter of well-known design such as an electrophysiology (EP) catheter used in EP studies by cardiologists. The catheter will be used for identifying the location of the S-A node cells 12. Cordis Corporation has manufactured a catheter with an expandable basket designed for such purposes. Location of the S-A node cells 12 is important in order to carry out the next essential process step which includes harvesting a mass of the S-A node cells.

In one version of the process, the mapping catheter merely is used to identify the S-A node cells 12 in order to ensure collection of an adequate mass of the S-A node cells 12 to carry out the further steps of the process. Preferably, however, the mapping catheter is selected so that it is capable of not only locating the S-A node cells but also is designed for identifying the boundaries of the S-A node cell knot 11. In the more preferred version of the process, the mapping catheter is manipulated by a physician to search the roof 13 of the interior wall in the atrium 11 to identify the entire area occupied by the S-A node cells 12. Location of these S-A node cells is possible because of the characteristic of the cells to generate small electrical signals which can be detected by mechanisms in the catheter. These signals can be directed to recording devices attached to the catheter. These recording devices record the location and the size of the area occupied by the S-A node cells 12 for future reference.

After the S-A node cells 12 are located, the mapping catheter is removed from the heart after which the next step is carried out. Another catheter is introduced into the right atrium 11 which is designed to remove a quantity of the S-A node cells 12 from the inside wall 13 of the right atrium 11. The preferred method of carrying out this step includes identification of healthy S-A node cells which have the greatest likelihood of generating a strong depolarization wave and also capable of being cultured after the cells have been removed from the right atrium 11.

Removal of the tissue sample from the S-A node 12 can be undertaken by a number of catheters well understood and known in the medical arts. Such catheters include small snipping devices capable of removing a small quantity of cells but without penetrating the thin wall 13 of the right atrium 11. Cordis Corporation manufactures a catheter of this type for intervenous biopsy.

Another catheter of the type which could be used for removing tissue cells includes a screw-type device designed to extract a sample of cells from myocardial tissue without creating severe damage to the surrounding tissue and which is also designed to avoid penetration of the atrium wall.

The S-A node cells are removed with the catheter from the right atrium after which the introducer is removed from the patient.

The next step in the process involves culturing the harvested quantity of S-A node cells in order to generate a larger quantity of healthy S-A node cells. Growth of human cells is currently a relatively well understood procedure which can take place in-vitro or, as an alternative, within the patient's body.

If the S-A node cells are to be grown in-vitro, the harvested S-A node cells are placed in a solution which includes sufficient combinations of nutrients, oxygen and similar elements necessary for the S-A node cells to reproduce. The in-vitro generation of additional S-A node cells will be carried out according to well understood principles of cell generation in temperature and other conditions which promote generation of healthy human cells.

Another method of generating new S-A node cells might also include reimplanting the cells in another location of the body. In this process, a surgeon would gain access to some other portion of a body where the S-A node cells can be implanted but where the cells will be adequately nourished by fluids, oxygen and a normal blood supply in the body. Generation of tissue in the body is known in the art.

The growth of the S-A node cells is monitored until the mass of cells grown is of sufficient magnitude to generate a depolarization wave capable of activating myocardial tissue. The critical mass of S-A node cells necessary to generate a viable depolarization wave may vary substantially from individual to individual and also may vary depending upon the condition of the myocardial tissue of the individual patient. It is therefore important that the growth of S-A node cells be carried out for a sufficient period to generate a mass of such cells which clearly are capable of generating a depolarization wave sufficient to activate even a severely diseased and inefficient heart muscle. The capacity to generate a very strong depolarization wave and which is greater than normal to activate a contraction in a normal heart will not injure the heart muscle. Experience from the use of electro-mechanical pacers has revealed that stimulation at energy levels far in excess of that which is normal by healthy S-A node cells does not seem to damage the surrounding heart tissue. The excess stimulating energy appears to be simply dissipated in the myocardial tissue with no ill effect. An inadequate depolarization wave, however, might result in irregular rhythm which would promote irregular heart beat. Accordingly, the depolarization wave which is generated by the newly grown S-A node cells should be sufficiently strong to adequately stimulate the myocardial tissue at a relatively high energy level.

After the critical mass of S-A node cells of sufficient quantity to generate a depolarization wave has been grown, the next process in the step is carried out. The critical mass of S-A node cells is then introduced by an implant catheter. Again, access to the interior of the heart is through the cephalic vein in the right shoulder of the patient. The catheter is directed with the critical mass of S-A node cells into the right ventricle of the heart. A catheter specifically designed to implant tissue is utilized in this step of the process and can be one of a number typically used in the medical field for such purposes. A catheter with a screw-type attachment such as those used for fixation in endocardial scew-in leads might be an example of one used to implant the critical mass of S-A node tissue in the right ventricle of the heart.

The catheter is directed into the right ventricle 19 of the heart where the critical mass of S-A node cells is implanted, preferably at the extreme apex of the right ventricle 19. This critical mass 27 of S-A node cells is illustrated in FIGURE 1 of the drawings where it is implanted at a site which is at the extreme apex of the right ventricle 19. Experience with electro-mechanical pacemakers has demonstrated that location of the stimulus for initiating depolarization waves is best located at the apex of the right ventricle 19. Depolarization initiation at that location ensures that the depolarization wave and, consequently, the contraction wave in the ventricular myocardium will begin at an optimum location and progress in an orderly fashion along the walls of the left and right ventricle to generate a contraction of the ventricle which is typical of a normal heart. The depolarization wave will progress from the critical mass 27 upwardly along the walls of the right ventricle and left ventricle as illustrated in FIGURE 1 of the drawings so that the ventricles contract, forcing blood out of the ventricles.

Thus, if the heart under treatment has damage to the A-V node 17, the Bundle of His 22 and/or bundle branches 23, 24 and 26, the depolarization wave generated by the critical mass of S-A node cells 27 will nevertheless begin the contraction at the apex of the heart to create a pumping action which is nearly identical to that of a normally operating heart. Thus, the failure of the other conduction elements of the heart are avoided.

The critical mass 27 of S-A node cells is preferably placed at the extreme apex of the right ventricle 19 of the heart. This location ensures an effective site from which a generated depolarization wave can radiate in a uniform and orderly progression along the walls 14 and 16 of the ventricles. Experience, however, has demonstrated that satisfactory function of the heart can be achieved if the critical mass 27 is located anywhere within the lower two-thirds of the right ventricle 19. The closer the implant site is to the tricuspid valve 28, the less effective the biological implant becomes. The generation of the depolarization wave higher up in the right ventricle 19 tends to produce a depolarization wave which does not spread throughout the heart muscle as effectively and with a rhythm which is as natural and effective as that of a properly operating heart. Nevertheless, while the location of the critical mass 27 at a different location within the lower two-thirds of the right ventricle 19 is less desirable, alternate location may be necessary if tissue at or near the apex of the right ventricle 19 is damaged or scarred.

As indicated in Drawing 1, the critical mass 27 of S-A node cells is implanted in the interior of the wall of the right ventricle 19 so that the critical mass 27 of S-A node tissues is constantly exposed to the fluids of the body as the fluids pass over the S-A node cells 27. This exposure of the S-A node cells to the fluids of the body in the right ventricle 19 ensures that the S-A node cell responds to the natural functions of the body. The S-A node cells respond to the level of oxygen and other chemicals in the blood and, accordingly, function in response to the various levels of such elements the same as they naturally functioned in the right atrium.

Consequently, a great advantage of the implant of a critical mass of S-A node cells at the apex of the right ventricle 19 is realized because these newly implanted S-A node cells will change the frequency of depolarization in response to body functions and activity demands. A serious disadvantage of most electro-mechanical pacemakers involves the feature or inability of such pacemakers to respond to increased demands on the heart. Increase in exercise of the organs of the body do not result in an increase in the pacing of the heart by most electro-mechanical pacemakers. The biological pacemaker represented by a critical mass of S-A node cells 27, on the other hand, do respond naturally to the increased or lowered demands of the body with the result that the S-A node cells implanted in the right ventricle function exactly the same as a natural pacemaker responding as needed to increase or decrease in the demands on the body organs.

Thus completed, the contemplated process provides a patient with a biological pacemaker which functions almost identically to the natural pacing of the heart except that the location of the depolarization initiator, the critical mass 27, is located in the right ventricle.

In most patients, an interruption or a defect in the pacing of the heart does not normally create immediate danger to the patient. As previously indicated, there are many sites of pacing cells in the heart and, when disease or blockage occurs which interrupts natural pacing, these secondary pacemakers undertake pacing of the heart sufficient to ensure a limited, although low, level of activity. This low level of activity of the heart will normally continue for a sufficient period of time so that the S-A node cells removed from the right atrium can be regrown for reimplantation. A preferred method of generation of the S-A node cells involves implantation of these cells in the patient's body where they are grown without change of the nutrients and other life support environment necessary for growth of these cells. Since the harvested cells come from the same patient, and then may be reimplanted in the patient, the process avoids many complications of typical electro-mechanical pacemaking devices, including that of tissue ejection and infection. If the patient's own S-A node cells are reimplanted, there is no danger that the S-A node cells will be identified as foreign tissue which the patient's immune system will attempt to destroy or reject.

While harvesting of S-A node cells from a patient and reimplant of the cells in the same patient is clearly the preferred method of undertaking this process, the process may nevertheless be carried out on differing individuals. An understanding of the immune process is at a sufficient high level so that harvesting of S-A node cells from a healthy individual for growth and implanting in another individual is reasonably possible. With proper tissue typing and subsequent suppression of the immune system, S-A node cells taken from a healthy individual or heart harvested from a deceased patient can be implanted as described in a diseased heart of another individual with a relatively high probability of success.

Experience with electro-mechanical pacemakers has also demonstrated that, on occasion, interference may occur between a site of new stimulation and the remaining functioning of the remaining S-A node cells. It is possible that the S-A node cells located in the right atrium are operating properly but with a diseased or interrupted conduction of the depolarization wave from the right atrium to the lower heart or the left and right ventricles. If the S-A node cells generated by culture are implanted in the apex of the right ventricle, these newly implanted S-A node cells may generate a depolarization wave which is not compatible or in synchronization with the depolarization wave generated by the healthy S-A node cells 12 located in the right atrium. In this case, the heart muscles will respond or attempt to respond to both depolarization waves with the result that the heart will operate ineffectively and may produce ineffective and insufficient pumping of the blood. In such cases, the S-A node cells in the right atrium should be destroyed. In this case, the process of this invention would include the additional step of destroying the S-A node cells in the right atrium.

If this step becomes necessary, the surgeon would remove the implant catheter from the introducer and then destroy the S-A cells of the right atrium. Destruction of the S-A node cells in the right atrium can be undertaken by several well known methods, including cryogenic destruction or destruction by electrical ablation. The destruction can be carried out by inserting a catheter of appropriate choice into the introducer where it is maneuvered into the right atrium. The location of the S-A node 12 is then identified from the previous record of location of the node 12 and the destruction of the cell is carried out through the indicated well-known methods. The entire bundle of S-A node cells 12 can be destroyed by reference to the previously mapped and recorded location of the cells in the right atrium. By previously recording or mapping the entire boundary of the S-A node cells 12, the procedure can be carried out to ensure that all such S-A node cells have been effectively destroyed and, thus, the site for spurious or unwanted depolarization wave generation can be removed from the heart.

Accordingly, after the process has been carried out as described, the critical mass 27 of S-A node cells provides a biological pacemaker which provides the tremendous advantages of responding to varying demands on the heart created by increase and decrease of exercise of the body. The newly implanted biological pacemaker responds to normal oxygen, hormonal and chemical changes in the blood with the result that the pacing of the heart is varied in accordance to demands placed on it. This results in more uniform and adequate function of other organs since the organs will be receiving varying rates of blood flow as needed by increased or decreased demands on those organs. Further, this biological pacemaker does not provide the disadvantages of exposure to mechanical failure which is typically present in the use of all electro-mechanical pacemakers.

In certain patients, the interruption of the depolarization and, therefore, contraction of the heart to form a natural heart beat is interrupted so severely that the normal heart beat cannot be sustained by alternate pacemaker cells throughout the heart. In these cases, the patient would be in severe stress or near death from heart stoppage if temporary pacing is not provided for the heart while the S-A node cells are grown. In these situations, mechanical implantation of a temporary electro-mechanical pacer may be necessary in order to temporarily sustain the proper function of the heart. Implementation of the electrode would be carried out at the time that the S-A node cells are harvested from the right atrium. After the S-A node cells are removed by the catheter used for harvesting the cells, the well-known technique of implanting an electro-mechanical pacemaker would then be undertaken. This implantation process is well known and well understood in the medical arts and, accordingly, requires no further explanation.

The implanted electro-mechanical pacemaker would be left in place while the S-A node cells are being grown. After the proper and critical mass of S-A node cells have been grown and are ready to be implanted in the patient, the implanted electrode would then be removed from the implantation site at the time that the critical mass of S-A node cells is implanted. The last step in this process would involve the removal of the pacemaker electrode after the S-A node cells have been properly positioned.

The above-described procedure is merely illustrative of the process of the present invention. Variations may be employed in the process without departing from the scope and principles of the invention. For example, a variety of means for destroying the S-A node cells in the right atrium might be employed, including destruction through electrical ablation. Further, location of the S-A node cell critical mass might be undertaken in a number of different locations in the lower portion of the right ventricle without departing from the principles of the invention. Location of the critical mass might be affected by the condition of the myocardial tissue in the various locations in the lower right ventricle. Location of the critical mass at or near the extreme apex of the right ventricle, while desirable, nevertheless can be varied in order to ensure proper generation of a useful depolarization wave. Avoidance of scar tissue in the myocardial tissue and similar defects in the myocardial tissue are to be avoided in the implant of the S-A node cells.

Further, the choice of catheters to carry out the various steps of the procedure is dictated only by the proper accomplishment of the particular process step. As indicated, a number of different catheters might be employed to harvest a mass of S-A node cells from the upper wall of the right atrium. Likewise, the exact style of the catheter used to map the boundaries of the S-A node cell may be varied and, yet, not depart from the process contemplated by the present invention. As an example, a catheter employing a basket-like series of electrodes might be employed in order to map the location of the boundaries of the S-A node site.

These and other variations may be employed without departing from the spirit and scope of the invention in which is claimed.

What is claimed is:

1. A method for providing for pacing of a human heart of a patient comprising:
   a. isolating a plurality of viable sino-atrial node cells from a human heart; and,
   b. implanting said plurality of viable sino-atrial node cells within said human heart, whereby said implanted viable sino-artial node cells pace said human heart.

2. A method according to claim 1 wherein said implanting step further comprises implanting said plurality of viable sino-atrial node cells within a ventricle of said human heart.

3. A method according to claim 2 wherein said implanting step further comprises implanting said plurality of viable sino-atrial node cells within the right ventricle of said human heart.

4. A method according to claim 3 wherein said implanting step further comprises implanting said plurality of viable sino-atrial node cells within the apex of said right ventricle of said human heart.

5. A method according to claim 4 wherein said plurality of viable sino-atrial node cells are from said patient.

6. A method according to claim 5 further comprising, after said isolating step and before said implanting step, removing said plurality of viable sino-atrial node cells from said patient.

7. A method according to claim 6 further comprising, after said removing step and before said implanting step, culturing said plurality of viable sino-atrial node cells.

8. A process for providing a biological pacemaker implant for the human heart which comprises the steps of:
   a. identifying S-A node cells in the right atrium of the heart;
   b. removing a quantity of said S-A node cells from the wall of the right atrium;
   c. culturing said quantity of S-A node cells to grow a quantity of said S-A node cell to produce a critical mass of said S-A node cells sufficient to generate a depolarization wave in myocardial tissue; and,
   d. implanting said critical mass of S-A node cells in the right ventricle of the heart to provide a depolarization wave of sufficient magnitude to stimulate contraction of the myocardial tissue of the ventricles of the heart to initiate and sustain substantially natural heartbeat.

9. A process in accordance with claim 8 in which the quantity of S-A node cells is removed from and implanted in the same heart.

10. A process in accordance with claim 8 in which culturing of said S-A node cells is carried out in-vitro and in a culture medium compatible with culture of myocardial tissue.

11. A process in accordance with claim 8 in which said quantity of S-A node cells is temporarily transplanted in a temporary site of the patient's body and in which said culturing takes place at said temporary site for a sufficient period of time to grow said critical mass of S-A node cells after which said critical mass of S-A node cells are removed from said temporary site for implanting in said right ventricle.

12. A process in accordance with claim 8 in which said critical mass of S-A node cells is implanted in the wall of the lower two thirds of the right ventricle.

13. A process in accordance with claim 8 in which said critical mass of S-A node cells is implanted at the apex of the myocardial tissues of the right ventricle of the heart.

14. A process in accordance with claim 8 which further includes the step of destroying the S-A node cells remaining in the right atrium to prevent generation of a depolarization wave out of synchronization with the depolarization wave generated by said implanted mass of S-A node cells.

15. A process in accordance with claim 14 in which said S-A node cells remained in said right atrium are cryogenically destroyed.

16. A process in accordance with claim 14 in which said S-A node cells remaining in said right atrium are destroyed through electrical ablation.

17. A process for providing a biological pacemaker implant for the human heart which comprises the steps of:
   a. inserting a mapping catheter into the right atrium of the heart;

b. mapping the site of the S-A node cells of the right atrium to determine the boundaries of the S-A node site and to identify the location of healthy S-A node cells;

c. removing a quantity of said healthy S-A node cells from the site of said S-A node cells in the right atrium;

d. culturing said quantity of S-A node cells to grow a quantity of said S-A node cell to produce a critical mass of said S-A node cells sufficient to generate a depolarization wave in myocardial tissue; and, e. implanting said critical mass of S-A node cells in the right ventricle of the heart to provide a depolarization wave of sufficient magnitude to stimulate contraction of the myocardial tissue of the ventricles of the heart to initiate and sustain substantially natural heartbeat.

18. A process in accordance with claim 17 in which the quantity of S-A node cells is removed from and implanted in the same heart.

19. A process in accordance with claim 17 which further includes the step of recording the boundaries of the site of the S-A node cells in the right atrium.

20. A process in accordance with claim 19 which further includes the steps of locating the site of the S-A node cells in said right atrium from said mapping of said sites and destroying the S-A node cells remaining in the right atrium to prevent generation of a depolarization wave in the right atrium.

21. A process in accordance with claim 17 in which said critical mass of S-A node cells is implanted at the apex of the myocardial tissues of the right ventricle of the heart.

22. A process in accordance with claim 17 in which said critical mass of S-A node cells is implanted in the wall of the lower two thirds of the right ventricle of the heart.

23. A process for providing a biological pacemaker implant for the human heart which comprises the steps of:

a. identifying S-A node cells int he right atrium of the heart;

b. removing a quantity of said S-A node cells from the wall of the heart;

c. implanting a pacemaker electrode in the right ventricle of the heart;

d. periodically inducing a depolarization wave in the myocardial tissue of the right ventricle through said electrode to promote a regular heartbeat function in the heart;

e. culturing said quantity of S-A node cells to grow a quantity of said S-A node cell to produce a critical mass of said S-A node cells sufficient to generate a depolarization wave in myocardial tissue;

f. implanting said critical mass of S-A node cells in the right ventricle of the heart to provide a depolarization wave of sufficient magnitude to stimulate contraction of the myocardial tissue of the ventricles of the heart to initiate and sustain substantially natural heartbeat of the heart; and, g. removing said pacemaker electrode from the right ventricle of the heart.

24. A process in accordance with claim 23 in which the quantity of S-A node cells is removed from and implanted in the same heart.

25. A process in accordance with claim 23 in which culturing of said S-A node cells is carried out in-vitro and in a culture medium compatible with culture of myocardial tissue.

26. A process in accordance with claim 23 in which said quantity of S-A node cells is temporarily transplanted in a temporary site of the patient's body and in which said culturing takes place at said temporary site for a sufficient period of time to grow said critical mass of S-A node cells after which said critical mass of S-A node cells are removed from said temporary site for implanting in said right ventricle.

27. A process in accordance with claim 23 in which said critical mass of S-A node cells is implanted in the wall of the lower two thirds of the right ventricle.

28. A process in accordance with claim 23 in which said critical mass of S-A node cells is implanted at the apex of the myocardial tissues of the right ventricle of the heart.

29. A process in accordance with claim 23 which further includes the step of destroying the S-A node cells remaining in the right atrium to prevent generation of a depolarization wave out of synchronization with the depolarization wave generated by said implanted mass of S-A node cells.

30. A process in accordance with claim 29 in which said S-A node cells remaining in said right atrium are cryogenically destroyed.

31. A process in accordance with claim 29 in which said S-A node cells remaining in said right atrium are destroyed through electrical ablation.

* * * * *